US007241739B2

(12) United States Patent
Valenzuela et al.

(10) Patent No.: US 7,241,739 B2
(45) Date of Patent: Jul. 10, 2007

(54) MORPHOGENIC PROTEIN

(75) Inventors: David M. Valenzuela, Yorktown Heights, NY (US); Eduardo A. Rojas, Tarrytown, NY (US); Aris N. Economides, New York, NY (US); Neil Stahl, Carmel, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 650 days.

(21) Appl. No.: 10/465,474

(22) Filed: Jun. 19, 2003

(65) Prior Publication Data

US 2003/0199042 A1    Oct. 23, 2003

Related U.S. Application Data

(62) Division of application No. 09/423,029, filed as application No. PCT/US98/06324 on Mar. 31, 1998, now Pat. No. 6,610,510.

(60) Provisional application No. 60/045,157, filed on Apr. 30, 1997, provisional application No. 60/044,427, filed on Apr. 29, 1997.

(51) Int. Cl.
*A61K 38/18* (2006.01)
*C07K 14/475* (2006.01)
(52) U.S. Cl. .......................... 514/12; 530/350
(58) Field of Classification Search ............... None
See application file for complete search history.

(56) References Cited

U.S. PATENT DOCUMENTS 6,133,232 A * 10/2000 De Robertis et al. ......... 514/12

OTHER PUBLICATIONS

U.S. Appl. No. 60/020,150.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Wozney JM. The bone morphogenetic protein family and osteogenesis. Mol Reprod Dev. Jun. 1992;32(2):160-7.*
Kingsley DM. The TGF-beta superfamily: new members, new receptors, and new genetic tests of function in different organisms. Genes Dev. Jan. 1994;8(2):133-46.*
DATABASE EMBL—EMEST13, Entry MMAA20122, ACC. No. AA120122, issued Nov. 21, 1996, Marra, M. et al., "mn32d09.r1 Beddington mouse embryonic region Mus musculus cDNA clone 538769 5'", XP-002072013.
Mechanisms of Development, vol. 68, issued Nov. 1997, "*Cerberus-like* is a secreted factor with neutralizing activity expressed in the anterior primitive endoderm of the mouse gastrula", pp. 45-57.

Developmental Biology, vol. 194, issued Feb. 15, 1998, Biben, C., et al., "Murine Cerberus Homologue mCer-1: A Candidate Anterior Patterning Molecule", pp. 121-132.
NATURE, vol. 382, issued Aug. 15, 1996, Bouwmeester, T., et al., "Cerberus is a head-inducing secreted factor expressed in the anterior endoderm of Spemann's organizer", pp. 547-549.
ONCOGENE, vol. 9, issued 1994, Enomoto, H., et al., "Identification of human DAN gene, mapping to the putative neuroblastoma tumor suppressor locus", pp. 2785-2791.
DEVELOPMENT, vol. 124, issued 1997, Furuta, Y., et al., "Bone morphogenetic proteins (BMPs) as regulators of dorsal forebrain development", pp. 2203-2212.
CELL, vol. 77, issued Apr. 22, 1994, Hemmati-Brivanlou, A., et al., "Follistatin, an Antagonist of Activin Is Expresses in the Spemann Organizer and Displays Direct Neutralizing Activity", pp. 283-295.
SCIENCE, vol. 262, issued Oct. 29, 1993, Lamb, T.M., et al., "Neural Induction by the Secreted Polypeptide Noggin", pp. 713-718.
Trends in Genetics, vol. 12, No. 12, issued Dec. 1996, Lemaire, P., et al., "The vertebrate organizer: structure and molecules", pp. 525-531.
CELL, vol. 81, issued Apr. 7, 1995, Lemaire, P., et al., "Expression Cloning of *Siamois*, a Xenopus Homeobox Gene Expressed in Dorsal-Vegetal Cells of Blastulae and Able to Induce A Complete Secondary Axis" pp. 85-94.
Jpn. J. Cancer Research, vol. 87, issued Jan. 1996, Ozaki, T., et al., "Cloning of Mouse *DAN* cDNA and Its Down-regulation in Transformed Cells".
CELL, vol. 86, issued Aug. 23, 1996, Piccolo, S., et al., "Dorsoventral Patterning in Xenopus: Inhibition of Ventral Signals by Direct Binding of Chordin to BMP-4", pp. 829-840.
Nature, vol. 376, issued Jul. 27, 1995, Sasai, Y., et al., "Regulation of neural induction by the Chd and Bmp-4 antagonistic patterning signals in Xenopus", pp. 333-336.
CELL, vol. 79, issued Dec. 2, 1994, Sasai, Y., et al., "Xenopus *chordin*:: A Novel Dorsalizing Factor Activated by Organizer-Specific Homeobox Genes", pp. 779-790.
NATURE, vol. 361, issued Feb. 11, 1993, Smith, W.C., et al., "Secreted *noggin* protein mimics the Spemann organizer in dorsalizing *Xenopus* mesoderm", pp. 547-549.
CELL, vol. 67, issued Nov. 15, 1991, Smith, W.C., and Harland, R.M., "Injected Xwnt-8 RNA Acts Early in Xenopus Embryos to Promotes Formation of a Vegetal Dorsalizing Center", pp. 752-765.
CELL, vol. 70, issued Sep. 4, 1992, Smith, W.C., and Harland, R.M., "Expression Cloning of noggin, a New Dorsalizing Factor Localized to the Spemann Organizer in Xenopus Embryos", pp. 829-840.
CELL, vol. 86, issued Aug. 23, 1996, Zimmerman, L.B., et al., "The Spemann Organizer Signal noggin Binds and Inactivates Bone Morphogenetic Protein 4", pp. 599-606.

* cited by examiner

*Primary Examiner*—David S. Romeo
(74) *Attorney, Agent, or Firm*—Valeta Gregg, Esq.

(57) ABSTRACT

Human Cerberus proteins and related nucleic acids are provided. Included are proteins comprising a human cerberus domain having specific activity, particularly the ability to antagonize a bone morphogenic protein. The proteins may be produced recombinantly from transformed host cells with the subject nucleic acids. Also provided are isolated hybridization probes and primers capable of specifically hybridizing with the disclosed genes, specific binding agents and methods of making and using the subject compositions.

3 Claims, 1 Drawing Sheet

MORPHOGENIC PROTEIN

This application is a divisional of U.S. application Ser. No. 09/423,029, filed Nov. 16, 1999, now U.S. Pat. No. 6,610,510, which is the National Stage of International Application No. PCT/US98/06324, filed Mar. 31, 1998, which claims the benefit of U.S. Provisional Application 60/045,157 filed Apr. 30, 1997, now abandoned, and U.S. Provisional Application 60/044,427 filed Apr. 29, 1997, now abandoned.

INTRODUCTION

1. Field of the Invention

The field of this invention is proteins which regulate cell function, and in particular, induce neural development or antagonize bone morphogenic proteins.

2. Background

Natural regulators of cellular growth, differentiation and function have provided important pharmaceuticals, clinical and laboratory tools, and targets for therapeutic intervention. A variety of such regulators have been shown to have profound effects on basic cellular differentiation and developmental pathways. For example, the recently cloned *Xenopus* cerberus protein induces the formation of head structures in anterior endoderm of vertebrate embryos. Similarly, the noggin protein induces head structures in vertebrate embryos, and can redirect mesodermal fates from ventral fates, such as blood and mesenchyme, to dorsal fates such as muscle and notochord and can redirect epidermal fates to anterior neural fates. The activities of chordin are similar to those of noggin, reflecting a common mechanism of action—namely antagonizing bone morphogenic proteins (BMP) and thereby preventing their function. BMPs have diverse biological activities in different biological contexts, including the induction of cartilage, bone and connective tissue, and roles in kidney, tooth, gut, skin and hair development.

Different members of the TGFβ superfamily can instruct cells to follow different fates, for example TGFβ induces neural crest to form smooth muscle, while BMP2 induces the same cells to become neurons. In *Xenopus* experiments, dissociated animal cap cells (prospective ectoderm) become epidermis in response to BMP4 but become mesoderm in response to activin.

Since the sequence identity between activin and BMP4 is low, it is not surprising that they induce different fates. It is more surprising that members of the BMP subfamily, which are quite closely related in sequence, can induce distinct fates. A striking example results from implantation of a matrix impregnated with a BMP into muscle; when the effects are monitored histologically, BMP2, 4 and 7 induce endochondral bone formation, whereas a related molecule BMP12/GDF7 induces connective tissue similar to tendon. Similarly, BMP4 can induce cell death in the hindbrain neural crest, while the related protein dorsalin does not.

Since different BMP family members can induce different fates, then BMP antagonists that have specificity in blocking subsets of BMPs could change the balance of BMPs that are presented to a cell, thus altering cell fate. In view of the importance of relative BMP expression in human health and disease, regulators of cellular function and BMP function in particular, such as noggin and cerberus, provide valuable reagents with a host of clinical and biotechnological applications. The present invention relates to a new family of regulators of cellular function.

Relevant Literature

Bouwmeester, T., et al. (1996) Nature 382: 595-601 describe cloning of the *Xenopus* cerberus gene and provide a deduced amino acid sequence of *Xenopus* cerberus protein in addition to describing its biological activity. Lamb, T. M., et al. (1993) Science 262: 713-718; Smith, W. C., et al. (1992) Cell 70: 829-840; Smith, W. C., et al. (1993) Nature 361: 547-549; and Zimmerman, L. B., et al. (1996) Cell 86: 599-606 describe the isolation and function of the noggin protein. Piccolo, S., et al. (1996) Cell 86: 589-598, Sasai, Y., et al. (1995) Nature 376: 333-336, and Sasai, Y., et al. (1994) Cell 79: 779-790 relate to the chordin protein. Enomoto et al. (1994) Oncogene 9: 2785-2791 and Ozaki, et al. (1996) Jpn. J. Cancer Res. 87: 58-61 describe human and murine homologs of the DAN gene.

SUMMARY OF THE INVENTION

The invention provides methods and compositions relating to human cerberus protein and related nucleic acids. Included are proteins comprising a human cerberus domain and having human cerberus-specific activity. The proteins may be produced recombinantly from transformed host cells with the subject nucleic acids. The invention provides binding agents such as specific antibodies, and methods of making and using the subject compositions in diagnosis (e.g., genetic hybridization screens for human cerberus transcripts), therapy (e.g., gene therapy to modulate human cerberus gene expression) and in the biopharmaceutical industry (e.g., reagents for screening chemical libraries for lead pharmacological agents).

Preferred uses for the subject human cerberus proteins include modifying the physiology of a cell comprising an extracellular surface by contacting the cell or medium surrounding the cell with an exogenous human cerberus protein under conditions whereby the added protein specifically interacts with a component of the medium and/or the extracellular surface to effect a change in the physiology of the cell. Also preferred are methods for screening for biologically active agents, which methods involve incubating a human cerberus protein in the presence of an extracellular human cerberus protein-specific binding target and a candidate agent, under conditions whereby, but for the presence of the agent, the protein specifically binds the binding target at a reference affinity; detecting the binding affinity of the protein to the binding target to determine an agent-biased affinity, wherein a difference between the agent-biased affinity and the reference affinity indicates that the agent modulates the binding of the protein to the binding target.

DETAILED DESCRIPTION OF THE INVENTION

Figure 1:
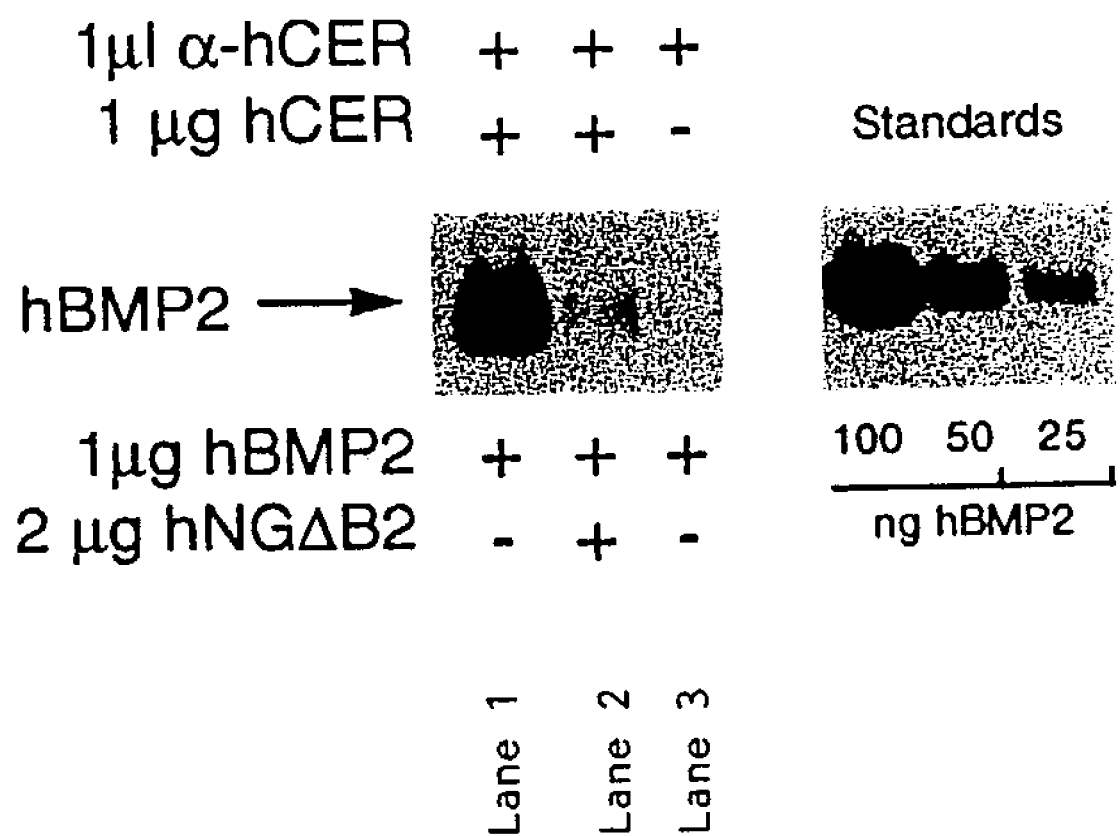
FIG. 1—Western Blot showing binding of human cerberus to human BMP2 in lane 1. Addition of a human noggin deletion mutein blocks binding of human cerberus to human BMP2 as shown in lane 2. Control for non-specific binding shown in lane 3.

The invention provides human cerberus protein which includes natural human cerberus protein and recombinant proteins comprising a human cerberus amino acid sequence, or a functional human cerberus protein domain thereof having an assay-discernable human cerberus-specific activity. Accordingly, the proteins may be deletion mutants of the disclosed natural human cerberus proteins and may be provided as fusion products, e.g., with non-human cerberus polypeptides. The subject human cerberus protein domains have human cerberus-specific activity or function and are functionally distinct from each other and from b57, DAN and noggin.

Without being bound by theory, we have formulated hypotheses about the embryological effects of cerberus based on where it is expressed, and on the effects of RNA injection in embryos. Since cerberus is expressed in the Spemann organizer, we believe cerberus to be a mediator of some of the effects of the Spemann organizer, such as neural induction. Since cerberus is expressed in regions that will become heart primordium, we believe cerberus to influence either the dorsal-ventral pattern or anterior-posterior pattern of the neural plate. In the frog, cerberus occupies the anteriormost endomesoderm. This localized expression of cerberus in the frog may give rise to heart primordium. Although cerberus is unable to dorsalize ventral mesoderm and does not rescue axis formation in ventralized frog embryos, it has been known to promote formation of anterior neural structures such as cement gland, brain, and olfactory placodes. Cerberus exhibits homology to b57, a protein that has been shown to directly bind BMP-2 and BMP-4 and inhibit their biological actions. This effect has also been shown to be mediated by the unrelated protein noggin which is also expressed in the Spemann organizer and which has been shown to induce neural ectoderm. By inference, cerberus may also be a direct inhibitor of BMP activity, and this may account for its known biological effects.

A number of applications for cerberus are suggested from its properties. Cerberus, like noggin and b57, may be useful in the study and treatment of heart disease and neurological disorders, as well as pathological conditions that arise from or involve heterotopic bone formation, cartilage or cartilagenous plaques. Furthermore, the cerberus cDNA may be useful as a diagnostic tool, such as through use of antibodies in assays for proteins in cell lines or use of oligonucleotides as primers in a PCR test to amplify those with sequence similarities to the oligonucleotide primer, and to see how much cerberus is present. The isolation of human cerberus, of course, also provides the key to isolate its putative receptor, other cerberus binding proteins, and/or study its antagonistic properties.

Human cerberus-specific activity or function may be determined by convenient in vitro, cell-based, or in vivo assays—e.g., in vitro binding assays, cell culture assays, in animals (e.g., immune response, gene therapy, transgenics, etc.), etc. Binding assays encompass any assay where the specific molecular interaction of a human cerberus protein with a binding target is evaluated. The binding target may be a natural binding target, or a non-natural binding target such as a specific immune protein such as an antibody, or a human cerberus specific agent such as those identified in assays described below. Generally, binding specificity is assayed by bioassay (e.g., the ability to induce neuronal tissue from injected embryonic ectoderm), TGFβ protein binding equilibrium constants (usually at least about $10^7$ M$^{-1}$, preferably at least about $10^8$ M$^{-1}$, more preferably at least about $10^9$ M$^{-1}$), by the ability of the subject protein to function as negative mutants in human cerberus-expressing cells, to elicit human cerberus specific antibody in a heterologous host (e.g., a rodent or rabbit), etc.

The claimed proteins may be isolated or pure—an "isolated" protein is one that is no longer accompanied by some of the material with which it is associated in its natural state, and that preferably constitutes at least about 0.5%, and more preferably at least about 5% by weight of the total protein in a given sample; a "pure" protein constitutes at least about 90%, and preferably at least about 99% by weight of the total protein in a given sample. The subject proteins and protein domains may be synthesized, produced by recombinant technology, or purified from cells. A wide variety of molecular and biochemical methods are available for biochemical synthesis, molecular expression and purification of the subject compositions, see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY). An exemplary method for isolating natural human cerberus protein involves expressing a cDNA library (e.g., one derived from *Xenopus* ovarian cells) and assaying expression products for embryonic axis formation. This method and other suitable bioassays amenable to detecting human cerberus proteins have been described by Lemaire, P., et al., (1995) Cell 81:85-94; Smith, W. C., and Harland, R. M. (1992) Cell 70: 829-40; Smith, W. C., and Harland, R. M. (1991) Cell 67: 753-765; Piccolo, S., et al., (1996) Cell 86: 589-98; and Zimmerman, L. B., et al., (1996) Cell 86: 599-606.

The subject proteins find a wide variety of uses including use as immunogens, targets in screening assays, bioactive reagents for modulating cell growth, differentiation and/or function, etc. For example, the invention provides methods for modifying the physiology of a cell comprising an extracellular surface by contacting the cell or medium surrounding the cell with an exogenous human cerberus protein under conditions whereby the added protein specifically interacts with a component of the medium and/or the extracellular surface to effect a change in the physiology of the cell. According to these methods, the extracellular surface includes plasma membrane-associated receptors; the exogenous human cerberus refers to a protein not made by the cell or, if so, expressed at non-natural levels, times or physiologic locales; and suitable media include in vitro culture media and physiological fluids such as blood, synovial fluid, etc. Effective administrations of subject proteins may be used to reduce undesirable (e.g., ectopic) bone formation, inhibit the growth of cells that require a morphogenic protein (e.g., BMP-dependent neuroblastomas and gliomas), alter morphogen-dependent cell fate/differentiation in culture, such as with cells for transplantation or infusion, etc. The proteins may be may be introduced, expressed, or repressed in specific populations of cells by any convenient way such as microinjection, promoter-specific expression of recombinant enzyme, targeted delivery of lipid vesicles, etc.

The invention provides natural and non-natural human cerberus-specific binding agents, methods of identifying and making such agents, and their use in diagnosis, therapy and pharmaceutical development. Human cerberus-specific binding agents include human cerberus-specific receptors, such as somatically recombined protein receptors like specific antibodies or T-cell antigen receptors (See, e.g., Harlow and Lane (1988) Antibodies, A Laboratory Manual, Cold Spring Harbor Laboratory) and also includes other natural binding agents identified with assays such as one-, two- and three-hybrid screens, and non-natural binding agents identified in screens of chemical libraries such as described below. Agents of particular interest modulate human cerberus function.

The invention provides human cerberus nucleic acids, which find a wide variety of applications including use as translatable transcripts, hybridization probes, PCR primers, diagnostic nucleic acids, etc., as well as use in detecting the presence of human cerberus genes and gene transcripts and in detecting or amplifying nucleic acids encoding additional human cerberus homologs and structural analogs.

The subject nucleic acids are of synthetic/non-natural sequences and/or are isolated, i.e., no longer accompanied by some of the material with which it is associated in its natural state, preferably constituting at least about 0.5%, more preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence disclosed herein and fragments thereof, contain such sequence or fragment at a terminus, immediately flanked by a sequence other than that to which it is joined on a natural chromosome, or flanked by a native flanking region fewer than 10 kb, preferably fewer than 2 kb, which is immediately flanked by a sequence other than that to which it is joined on a natural chromosome. While the nucleic acids are usually RNA or DNA, it is often advantageous to use nucleic acids comprising other bases or nucleotide analogs to provide modified stability, etc.

The amino acid sequences of the disclosed human cerberus protein is used to back translate human cerberus protein-encoding nucleic acids optimized for selected expression systems (Holler, et al. (1993) Gene 136: 323-328; Martin, et al. (1995) Gene 154: 150-166) or used to generate degenerate oligonucleotide primers and probes for use in the isolation of natural human cerberus encoding nucleic acid sequences ("GCG" software, Genetics Computer Group, Inc., Madison, Wis.). Human cerberus encoding nucleic acids may be part of expression vectors and may be incorporated into recombinant host cells, e.g., for expression and screening, for transgenic animals, for functional studies such as the efficacy of candidate drugs for disease associated with human cerberus mediated signal transduction, etc. Expression systems are selected and/or tailored to effect human cerberus protein structural and functional variants through alternative post-translational processing.

The invention also provides for nucleic acid hybridization probes and replication/amplification primers having a human cerberus cDNA specific sequence and sufficient to effect specific hybridization with SEQ. NO. 1. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Human cerberus cDNA homologs can also be distinguished from other protein using alignment algorithms, such as BLASTX (Altschul, et al. (1990) Basic Local Alignment Search Tool, J. Mol. Biol. 215: 403-410).

Human cerberus hybridization probes find use in identifying wild-type and mutant alleles in clinical and laboratory samples. Mutant alleles are used to generate allele-specific oligonucleotide (ASO) probes for high-throughput clinical diagnoses. Human cerberus nucleic acids are also used to modulate cellular expression or intracellular concentration or availability of active human cerberus. Human cerberus inhibitory nucleic acids are typically antisense—single stranded sequences comprising complements of the disclosed natural human cerberus coding sequences. Antisense modulation of the expression of a given human cerberus protein may employ antisense nucleic acids operably linked to gene regulatory sequences. Cells are transfected with a vector comprising a human cerberus sequence with a promoter sequence oriented such that transcription of the gene yields an antisense transcript capable of binding to endogenous human cerberus encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given human cerberus protein may be administered to the target cell, in or temporarily isolated from a host, at a concentration that results in a substantial reduction in expression of the targeted protein. An enhancement in human cerberus expression is effected by introducing into the targeted cell type human cerberus nucleic acids which increase the functional expression of the corresponding gene products. Such nucleic acids may be human cerberus expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of human cerberus modulatable cellular function. Generally, these screening methods involve assaying for compounds which modulate human cerberus interaction with a natural human cerberus binding target. A wide variety of assays for binding agents are provided including protein-protein binding assays, immunoassays, cell based assays, etc. Preferred methods are amenable to automated, cost-effective high throughput screening of chemical libraries for lead compounds.

In vitro binding assays employ a mixture of components including a human cerberus protein, which may be part of a fusion product with another peptide or polypeptide, e.g., a tag for detection or anchoring, etc. The assay mixtures comprise a natural human cerberus binding target. While native binding targets may be used, it is frequently preferred to use portions thereof as long as the portion provides binding affinity and avidity to the subject human cerberus conveniently measurable in the assay. The assay mixture also comprises a candidate pharmacological agent. Candidate agents encompass numerous chemical classes, though typically they are organic compounds, preferably small organic compounds, and are obtained from a wide variety of sources including libraries of synthetic or natural compounds. A variety of other reagents such as salts, buffers, neutral proteins, e.g., albumin, detergents, protease inhibitors, nuclease inhibitors, antimicrobial agents, etc., may also be included. The mixture components can be added in any order that provides for the requisite bindings and incubations may be performed at any temperature which facilitates optimal binding. The mixture is incubated under conditions whereby, but for the presence of the candidate pharmacological agent, the human cerberus specifically binds the cellular binding target, portion or analog with a reference binding affinity. Incubation periods are chosen for optimal binding but are also minimized to facilitate rapid, high throughput screening.

After incubation, the agent-biased binding between the human cerberus and one or more binding targets is detected by any convenient way. For cell-free binding type assays, a separation step is often used to separate bound from unbound components. Separation may be effected by precipitation, immobilization, etc., followed by washing by, e.g., membrane filtration or gel chromatography. For cell-free binding assays, one of the components usually comprises or is coupled to a label. The label may provide for direct detection as radioactivity, luminescence, optical or electron density, etc., or indirect detection such as an epitope tag, an enzyme, etc. A variety of methods may be used to detect the label depending on the nature of the label and other assay components, e.g., through optical or electron density, radiative emissions, nonradiative energy transfers, or indirectly detected with antibody conjugates, etc. A difference in the binding affinity of the human cerberus protein to the target in the absence of the agent as compared with the binding affinity in the presence of the agent indicates that the agent modulates the binding of the human cerberus protein to the corresponding binding target. A difference, as used herein, is statistically significant and preferably represents at least a 50%, more preferably at least a 90% difference.

The invention provides for a method for modifying the physiology of a cell comprising an extracellular surface in contact with a medium, said method comprising the step of contacting said medium with an exogenous human cerberus protein under conditions whereby said protein specifically interacts with at least one of said medium and said extracellular surface to effect a change in the physiology of said cell.

The invention further provides for a method for screening for biologically active agents, said method comprising the steps of a) incubating a human cerberus protein in the presence of an extracellular human cerberus protein specific binding target and a candidate agent, under conditions whereby, but for the presence of said agent, said protein specifically binds said binding target at a reference affinity; b) detecting the binding affinity of said protein to said binding target to determine an agent-biased affinity, wherein a difference between the agent-biased affinity and the reference affinity indicates that said agent modulates the binding of said protein to said binding target.

One embodiment of the invention is an isolated human cerberus protein comprising the amino acid sequence as set forth herein or a fragment thereof having human cerberus-specific activity.

Another embodiment of the invention is a recombinant nucleic acid encoding human cerberus protein comprising the amino acid sequence as set forth herein or a fragment thereof having human cerberus-specific activity.

Still another embodiment is an isolated nucleic acid comprising a nucleotide sequence as set forth herein or a fragment thereof having at least 18 consecutive bases and sufficient to specifically hybridize with a nucleic acid having the sequence of set forth herein in the presence of natural human cerberus cDNA.

Applicants have devised a method of screening for a molecule capable of competing with human cerberus for binding to a BMP comprising:
  a) contacting a sample suspected of containing the molecule with the BMP in the presence of human cerberus under conditions in which the human cerberus is capable of binding to the BMP; and b) detecting binding of the molecule to the BMP. In a preferred embodiment, the human cerberus is detectably labeled and includes, but is not limited to, human cerberus linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

By way of nonlimiting example, the method may be performed via an assay which is conceptually similar to an ELISA assay. For example, a BMP may be bound to a solid support, such as a plastic multiwell plate. As a control, a known amount of a molecule which contains the human cerberus BMP-binding domain and which has been Myc-tagged may then be introduced to the well and any tagged molecules which bind the BMP may then be identified by means of a reporter antibody directed against the Myc-tag. This assay system may then be used to screen test samples for molecules which are capable of i) binding to the tagged molecule or ii) binding to the BMP and thereby blocking binding to the BMP by the tagged molecule. For example, a test sample containing a putative molecule of interest together with a known amount of a tagged molecule which contains the human cerberus BMP-binding domain may be introduced to the well and the amount of tagged molecule which binds to the BMP may be measured. By comparing the amount of bound tagged molecule in the test well to the amount in the control well, samples containing molecules which are capable of blocking tagged molecule binding to the BMP may be identified. The molecules of interest thus identified may be isolated using methods well known to one of skill in the art.

Once a blocker of BMP binding is found, one of skill in the art would know to perform secondary assays to determine whether the blocker is binding to the tagged molecule or to the BMP, as well as assays to determine if the blocker molecule can neutralize the biological activity of the bound molecule.

The present invention also provides for antibodies to the human cerberus protein described herein which are useful for detection of the protein in, for example, diagnostic applications. For preparation of monoclonal antibodies directed toward this human cerberus protein, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77-96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g. Teng et al., 1983, Proc. Natl. Acad. Sci. U.S.A. 80:7308-7312; Kozbor et al., 1983, Immunology Today 4:72-79; Olsson et al., 1982, Meth. Enzymol. 92:3-16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the human cerberus protein described herein. For the production of antibody, various host animals can be immunized by injection with the human cerberus protein, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected human cerberus protein epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g. immunoabsorption or immunoaffinity chromatography, chromatographic methods such as HPLC (high performance liquid chromatography), or a combination thereof.

The invention further provides for a method of using a human cerberus protein or fragment thereof as an antagonist of the activity of a bone morphogenic protein (BMP). Preferably, the invention provides for a method of antagonizing the function of a Bone Morphogenic Protein (BMP) which comprises contacting said BMP with human cerberus protein or a fragment thereof. The method of the invention is carried out under conditions whereby the human cerberus or fragment thereof binds to the BMP. In further preferred embodiments of the invention, the human cerberus or fragment thereof is used to antagonize the function of BMP2 or BMP4.

Antagonists to BMPs may be useful for preventing and treating BMP-related disorders of animals, especially of humans. It was, therefore, an object of this invention to identify substances which effectively antagonize the function of BMPs in disease states in animals, preferably mammals, especially in humans. It was another object of this invention to prepare novel compounds which inhibit BMP. It was still another object of this invention to develop a method of antagonizing the functions of BMPs in disease states in mammals. It was also an object of this invention to develop a method of preventing or treating disorders relating to the function of BMPs.

In addition to their roles in normal bone formation, the BMPs appear to be involved in diseases in which they promote abnormal bone growth. For example, BMPs have been reported to play a causative role in the disease known as Fibrodysplasia Ossificans Progressiva (FOP), in which patients grow an abnormal "second skeleton" that prevents any movement.

Therefore, an object of the present invention is to provide a novel molecule for the treatment of diseases or disorders including, but not limited to, Fibrodysplasia Ossificans Progressiva (FOP). Since human cerberus binds BMPs, it offers hope as a therapeutic agent for this disease. Additionally, abnormal bone growth can occur after hip replacement surgery and thus ruin the surgical outcome. This is a more common example of pathological bone growth and a situation in which binders of BMPs such as human cerberus may be therapeutically useful. Human cerberus may also be useful for treating other forms of abnormal bone growth, such as the pathological growth of bone following trauma, burns or spinal cord injury. In addition, human cerberus may be useful for treating or preventing the undesirable actions of BMPs associated with the abnormal bone growth seen in connection with metastatic prostate cancer or osteosarcoma.

In additional embodiments, the human cerberus nucleic acids, proteins, fragments and peptides of the invention may be used to antagonize BMP activity in mammals.

The present invention also provides for compositions comprising a human cerberus molecule, as described herein and a suitable carrier. The active ingredient, which may comprise the human cerberus, should be formulated in a suitable carrier for systemic or local administration in vivo by any appropriate route including, but not limited to injection (e.g., intravenous, intraperitoneal, intramuscular, subcutaneous, endoneural, perineural, intraspinal, intraventricular, intravitreal, intrathecal etc.), by absorption through epithelial or mucocutaneous linings (e.g., oral mucosa, rectal and intestinal mucosa, etc.); or by a sustained release implant, including a cellular or tissue implant.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems.

The following examples are offered by way of illustration and not by way of limitation.

EXAMPLE 1

Cloning and Sequencing of Human Cerberus Gene

A human genomic library (Genome Systems, Inc.—Human release II BAC-4435) was hybridized to a mouse probe approximately 314 nucleotides in length that was obtained by PCR from a mouse EST clone (GenBank accession number AA120122; clone number 538769). DNA from human clones hybridizing to the mouse probe was digested with restriction enzymes, Southern blotted and hybridized. Those DNA fragments hybridizing to the mouse probe were purified, then subcloned using a commercial cloning kit (Zero Blunt PCR Cloning Kit, Invitrogen Cat# K2700-20) and sequenced using the ABI 373A DNA sequencer and Taq Dideoxy Terminator Cycle Sequencing Kit (Applied Biosystems, Inc., Foster City, Calif.). The sequence obtained corresponded to a segment of human cerberus encoding a polypeptide starting from the amino acid Threonine at position 170 (see SEQ ID No. 2) to a point beyond the stop codon. The RACE procedure was then used to obtain the full length human cerberus nucleotide sequence as follows. Oligonucleotides were designed based on the partial human sequence and used as primers for the reverse transcriptase reaction and for PCR. An approximately 1.2 Kb fragment was isolated and sequenced and found to contain the remainder of the human cerberus sequence. The sequence of human cerberus (SEQ ID NO. 1) was then further confirmed by PCR and by sequencing of a full length cerberus cDNA and also by partial direct sequencing of the human genomic clone described above.

EXAMPLE 2

Construction of Human Cerberus (hCer) Expression Plasmid pRG629

A DNA fragment encoding the gene for hCerberus was PCR amplified from pMT21.hCer.Fc using the primers N1-hCer (5'-AAACATGATGCAGGATGG CCGCCAG-3') and C1-hCer (5'-GAGAGCGGCCGCTCATTAAGCT-GAAACT CCTGGGATAAAGGAATCCTGGG-3'). The resulting 769 bp fragment was digested with Not 1 then ligated into the Pme 1-Not 1 sites of pRG461 a high copy vector encoding the gene for kanamycin resistance. This vector contains the phage T7 Φ1.1 promoter which directs the transcription of genes inserted into the Pme1 site. pRG461 was constructed at Regeneron. A clone was identified and named pRG629, the construct was confirmed by DNA sequence analysis, then transformed into $E.$ $coli$ strain RFJ143 by electroporation. RFJ143 is an $E.$ $Coli$ strain constructed at Regeneron and is essentially $E.$ $coli$ K12 strain W3110 lacIQ ZpL8 Z+Y+fhuAΔ322-405 ara (DE3).

EXAMPLE 3

Purification of Human Cerberus Protein $E.$ $coli$ strain RFJ143 containing pRG629 was grown in LB medium (Difco) and expression of hCerberus was induced by the addition of 1 mM IPTG. Induced cells were collected by centrifugation, resuspended in 10 volumes of 100 mM Tris-HCl, pH 8.5, 20 mM EDTA, and lysed by passage through a Niro-Soave Panda cell disrupter (Niro-Soave) to release inclusion bodies. The cell lysate was centrifuged and the pellet was resuspended in 10 volumes of 6 M guanidinium-HCl, 100 mM Tris-HCl, pH 8.5, 10 mM EDTA, 100 mM Na2SO3, 10 mM Na2S4O6 and stirred for 16 hr at room temperature. The solubilized inclusion bodies were fractionated on a Sephacryl S-300 column (Pharmacia) equilibrated in 8 M urea, 50 mM Tris-HCl, pH 8.0, 200 mM NaCl, 1 mM EDTA. Fractions containing hCerberus were pooled, diluted with 4 volumes of 6 M urea, 20 mM MES (2-(N-Morpholino)ethanesulfonic acid), pH 6.0 then loaded onto an SP-Sepharose (Pharmacia) column equilibrated with 6 M urea, 20 mM MES, pH 6.0 and eluted from the column with a linear gradient of NaCl in 6 M urea, 20 mM MES, pH 6.0. Purified cerberus was refolded by dilution with 10 volumes of buffer to 3.5 M urea, 50 mM Tris-HCl, pH 8.5, 0.1 mM EDTA, 0.5 mM cysteine followed by incubation at 4° C. After 2 days incubation, the refold mix was loaded onto a Q-Sepharose column (Pharmacia) equilibrated with 4 M urea, 50 mM Tris-HCl, pH 9.5, 0.1 mM EDTA, 20% glycerol ad eluted with a linear NaCl gradient in the same buffer. Fractions containing hCerberus were pooled and dialyzed against 20 mM Tris-HCl, pH 8.0, 150 mM NaCl, 0.1 mM EDTA. The dialysate was acidified with 0.1% TFA, loaded onto a Jupiter C5 column (Phenomenex) equilibrated in 0.1% TFA, 10% acetonitrile, and eluted with an increasing acetonitrile gradient from 30% to 50% at 1.3%/min. Fractions containing hCerberus were pooled, dried under vacuum, then resuspended in 20 mM Tris-HCl, pH 8.0, 150 mM NaCl, 0.1 mM EDTA.

EXAMPLE 4

Demonstration That Human Cerberus Binds to Human BMP2

Human Cerberus (1 µg/ml) that was expressed in $E.$ $coli$ and refolded was co-incubated with hBMP2 (1 µg/ml) in the absence or in the presence of human noggin protein (hNGΔB2, 2 µg/ml). Human noggin binds to BMP2 with high affinity. The hNGΔB2 is a deletion mutein of human noggin that displays identical biological activity to human noggin but has reduced binding to heparin. Thus addition of noggin (hNGΔB2) should inhibit binding of hCER to BMP2, if an excess of noggin is added over hCER and BMP2.

The formation of a stable complex between hCER and the BMPs was determined by immunoprecipitating hCER and associated proteins using an anti-hCER antisera bound to Protein G-Sepharose beads (Pharmacia). The binding reaction was carried out in binding buffer, which is comprised of 20 mM Tris pH 7.6, 150 mM NaCl, 0.1% Tween 20 (TBST), 1 mg/ml bovine serum albumin (BSA). Binding was allowed to proceed for 1 hour, at 25° C., in a reaction volume of 1 ml, with continuous mixing to keep the Protein G-Sepharose in suspension, after which point the beads were spun down, washed once with TBST, moved to new eppendorf tubes, and washed 3 more times with TBST. Proteins bound to the beads were solubilized by addition of 25 µl of Laemmli SDS-PAGE sample buffer (see Sambrook, et al.—A Cloning Manual, Cold Spring Harbor Laboratory) and loaded onto 4 to 12% NuPAGE/MES gradient gels (Novex), which were run under reducing conditions. The proteins were subsequently transferred on Immobilon P (Millipore) and Western blotted for the presence of BMP2 or BMP4 using polyclonal antisera raised against the respective proteins.

As can be seen in FIG. 1, hCER binds to hBMP2 (lane 1). Addition of hNGΔB2 blocks this interaction (lane 2), by binding to hBMP2 and blocking its ability to bind to hCER. This indicates that the epitope recognized by hCER on hBMP2 is the same or overlaps with the epitope recognized by noggin, or alternatively that binding of noggin to BMP2 and BMP4 sterically hinders the binding of hCER. There was no binding of hBMP2 to the beads if hCER was omitted from the reaction (lane 3), indicating that there is no non-specific binding of hBMP2 to the beads and that the observed binding is hCER-dependent. It should be noted that identical results have been obtained when examining the interaction of hCER with BMP4 and also when using different tagged forms of hCER, such as hCER-FLAG, hCER-myc and hCER-Fc. The tagged forms may be produced using standard genetic engineering techniques (see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY).

EXAMPLE 5

Tissue Expression of Human Cerberus

We have examined the expression of human Cerberus by analysis of polyA+ mRNA prepared from different adult human tissues. TABLE 1 lists the tissues tested and the relative level of expression of hCerberus detected in these tissues.

TABLE 1

| TISSUE | Relative Level of Expression of hCER |
|---|---|
| heart | undetectable |
| brain | undetectable |
| placenta | undetectable |
| lung | undetectable |
| liver | undetectable |
| skeletal muscle | undetectable |
| kidney | undetectable |
| pancreas | undetectable |
| spleen | undetectable |
| thymus | undetectable |
| prostate | undetectable |
| testis | undetectable |
| ovary | undetectable |
| small intestine | medium |
| colon (mucosa lining) | low |
| peripheral blood leukocytes | undetectable |
| stomach | high |
| thyroid | very low |
| spinal chord | very low |
| lymph node | medium |
| trachea | undetectable |
| adrenal gland | undetectable |
| bone marrow | undetectable |
| skeletal (muscle only) | undetectable |
| uterus (no endometrium) (muscle only) | low |
| colon (no mucosa) (muscle only) | very low |
| small intestine (muscle only) | high (highest of all tissues screened) |
| bladder (muscle only) | undetectable |
| heart (muscle only) | undetectable |
| stomach (muscle only) | high |
| prostate (muscle only) | undetectable |

REFERENCES

Bouwmeester, T., Kim, S. H., Sasai, Y., Lu, B., and De, R. E. M. (1996). Cerberus is a head-inducing secreted factor expressed in the anterior endoderm of Spemann's organizer. Nature 382, 595-601.

Furuta, Y., Piston, D. W., and Hogan, B. L. (1997). Bone morphogenetic proteins (BMPs) as regulators of dorsal forebrain development. Development 124, 2203-12.

Hemmati-Brivanlou, A., Kelly, O. G., and Melton, D. A. (1994). Follistatin, an antagonist of activin, is expressed in the Spemann organizer and displays direct neuralizing activity. Cell 77, 283-95.

Piccolo, S., Sasai, Y., Lu, B., and De, R. E. M. (1996). Dorsoventral patterning in *Xenopus*: Inhibition of ventral signals by direct binding of chordin to BMP-4. Cell 86, 589-598.

Smith, W. C., and Harland, R. M. (1992). Expression cloning of noggin a new dorsalizing factor localized to the spemann organizer in *xenopus* embryos. Cell 70, 829-840.

Zimmerman, L. B., Jesus, E. J. M. D., and Harland, R. M. (1996). The Spemann organizer signal noggin binds and inactivates bone morphogenetic protein 4. Cell 86, 599-606.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
Human cerberus nucleotide sequence
                                                               SEQ ID No. 1
             10          20          30          40          50          60
ATG CAT CTC CTC TTA TTT CAG CTG CTC GTA CTC CTG CCT CTA GGA AAG ACC ACA CGG CAC CAG GAT 70          80          90         100         110         120         130
GGC CGC CAG AAT CAG AGT TCT CTT TCC CCC GTA CTC CTG CCA AGG AAT CAA AGA GAG CTT CCC ACA 140         150         160         170         180         190
GGC AAC CAT GAG GAA GCT GAG GAG AAG CCA GAT CTG TTT GTC GCA GTG CCA CAC CTT GTA GGC ACC 200         210         220         230         240         250         260
AGC CCT GCA GGG GAA GGC CAG AGG CAG AGA GAG AAG ATG CTG TCC AGA TTT GGC AGG TTC TGG AAG 270         280         290         300         310         320         330
AAG CCT GAG AGA GAA ATG CAT CCA TCC AGG GAC TCA GAT AGT GAG CCC TTC CCA CCT GGG ACC CAG 340         350         360         370         380         390
TCC CTC ATC CAG CCG ATA GAT GGA ATG AAA ATG GAG AAA TCT CCT CTT CGG GAA GAA GCC AAG AAA 400         410         420         430         440         450         460
TTC TGG CAC CAC TTC ATG TTC AGA AAA ACT CCG GCT TCT CAG GGG GTC ATG TTG CCC ATG AAA AGC 470         480         490         500         510         520
CAT GAA GTA CAT TGG GAG ACC TGC AGG ACA GTG CCC TTC AGC CAG ACT ATA ACC CAC GAA GGC TGT 530         540         550         560         570         580         590
GAA AAA GTA GTT GTT CAG AAC AAC CTT TGC TTT GGG AAA TGC GGG TCT GTT CAT TTT CCT GGA GCC 600         610         620         630         640         650         660
GCG CAG CAC TCC CAT ACC TCC TGC TCT CAC TGT TTG CCT GCC AAG TTC ACC ACG ATG CAC TTG CCA 670         680         690         700         710         720
CTG AAC TGC ACT GAA CTT TCC TCC GTG ATC AAG GTG GTG ATG CTG GTG GAG GAG TGC CAG TGC AAG
```

```
                    730          740          750          760          770          780          790
                    GTG AAG ACG GAG CAT GAA GAT GGA CAC ATC CTA CAT GCT GGC TCC CAG GAT TCC TTT ATC CCA GGA

800
                    GTT TCA GCT TGA
```

HUMAN CERBERUS amino acid sequence.

SEQ ID No. 2

```
                                          10                                            20
                    Met His Leu Leu Leu Phe Gln Leu Leu Val Leu Leu Pro Leu Gly Lys Thr Thr Arg His Gln Asp 30                                       40
                    Gly Arg Gln Asn Gln Ser Ser Leu Ser Pro Val Leu Leu Pro Arg Asn Gln Arg Glu Leu Pro Thr 50                                     60
                    Gly Asn His Glu Glu Ala Glu Glu Lys Pro Asp Leu Phe Val Ala Val Pro His Leu Val Ala Thr 70                                    80
                    Ser Pro Ala Gly Glu Gly Gln Arg Gln Arg Glu Lys Met Leu Ser Arg Phe Gly Arg Phe Trp Lys 90                                       100                                     110
                    Lys Pro Glu Arg Glu Met His Pro Ser Arg Asp Ser Asp Ser Glu Pro Phe Pro Pro Gly Thr Gln 120                                   130
                    Ser Leu Ile Gln Pro Ile Asp Gly Met Lys Met Glu Lys Ser Pro Leu Arg Glu Glu Ala Lys Lys 140                                    150
                    Phe Trp His His Phe Met Phe Arg Lys Thr Pro Ala Ser Gln Gly Val Ile Leu Pro Ile Lys Ser 160                                     170
                    His Glu Val His Trp Glu Thr Cys Arg Thr Val Pro Phe Ser Gln Thr Ile Thr His Glu Gly Cys 180                                    190
                    Glu Lys Val Val Val Gln Asn Asn Leu Cys Phe Gly Lys Cys Gly Ser Val His Phe Pro Gly Ala 200                                           210                                  220
                    Ala Gln His Ser His Thr Ser Cys Ser His Cys Leu Pro Ala Lys Phe Thr Thr Met His Leu Pro 230                                    240
                    Leu Asn Cys Thr Glu Leu Ser Ser Val Ile Lys Val Val Met Leu Val Glu Glu Cys Gln Cys Lys 250                                     260
                    Val Lys Thr Glu His Glu Asp Gly His Ile Leu His Ala Gly Ser Gln Asp Ser Phe Ile Pro Gly

267
                    Val Ser Ala
```

---

What is claimed is:

1. An isolated human cerberus protein comprising the amino acid sequence of SEQ ID NO: 2.

2. A composition comprising the human cerberus protein of claim 1, and a pharmaceutically acceptable carrier.

3. An isolated human cerberus protein encoded by a nucleic acid sequence selected from the group consisting of:

a) a nucleotide sequence comprising the coding region of the human cerberus nucleic acid molecule as set forth in SEQ ID NO: 1;
b) a nucleotide sequence that, due to the degeneracy of the genetic code, differs from the nucleotide sequence of (a) and encodes human cerberus as set forth in SEQ ID NO:2.

* * * * *

SEQUENCE LISTING

```
<160> NUMBER OF SEQ ID NOS: 4

<210> SEQ ID NO 1
<211> LENGTH: 804
<212> TYPE: DNA
<213> ORGANISM: Homo sapiens
<220> FEATURE:
<221> NAME/KEY: CDS
<222> LOCATION: (1)..(801)

<400> SEQUENCE: 1 atg cat ctc ctc tta ttt cag ctg ctg gta ctc ctg cct cta gga aag         48
Met His Leu Leu Leu Phe Gln Leu Leu Val Leu Leu Pro Leu Gly Lys
1               5                   10                  15 acc aca cgg cac cag gat ggc cgc cag aat cag agt tct ctt tcc ccc         96
Thr Thr Arg His Gln Asp Gly Arg Gln Asn Gln Ser Ser Leu Ser Pro
            20                  25                  30 gta ctc ctg cca agg aat caa aga gag ctt ccc aca ggc aac cat gag        144
Val Leu Leu Pro Arg Asn Gln Arg Glu Leu Pro Thr Gly Asn His Glu
        35                  40                  45 gaa gct gag gag aag cca gat ctg ttt gtc gca gtg cca cac ctt gta        192
Glu Ala Glu Glu Lys Pro Asp Leu Phe Val Ala Val Pro His Leu Val
```

```
                    50                    55                    60
gcc  acc  agc  cct  gca  ggg  gaa  ggc  cag  agg  cag  aga  gag  aag  atg  ctg    240
Ala  Thr  Ser  Pro  Ala  Gly  Glu  Gly  Gln  Arg  Gln  Arg  Glu  Lys  Met  Leu
65                       70                        75                       80 tcc  aga  ttt  ggc  agg  ttc  tgg  aag  aag  cct  gag  aga  gaa  atg  cat  cca    288
Ser  Arg  Phe  Gly  Arg  Phe  Trp  Lys  Lys  Pro  Glu  Arg  Glu  Met  His  Pro
                         85                        90                       95 tcc  agg  gac  tca  gat  agt  gag  ccc  ttc  cca  cct  ggg  acc  cag  tcc  ctc    336
Ser  Arg  Asp  Ser  Asp  Ser  Glu  Pro  Phe  Pro  Pro  Gly  Thr  Gln  Ser  Leu
                    100                      105                      110 atc  cag  ccg  ata  gat  gga  atg  aaa  atg  gag  aaa  tct  cct  ctt  cgg  gaa    384
Ile  Gln  Pro  Ile  Asp  Gly  Met  Lys  Met  Glu  Lys  Ser  Pro  Leu  Arg  Glu
               115                      120                      125 gaa  gcc  aag  aaa  ttc  tgg  cac  cac  ttc  atg  ttc  aga  aaa  act  ccg  gct    432
Glu  Ala  Lys  Lys  Phe  Trp  His  His  Phe  Met  Phe  Arg  Lys  Thr  Pro  Ala
          130                      135                      140 tct  cag  ggg  gtc  atc  ttg  ccc  atc  aaa  agc  cat  gaa  gta  cat  tgg  gag    480
Ser  Gln  Gly  Val  Ile  Leu  Pro  Ile  Lys  Ser  His  Glu  Val  His  Trp  Glu
145                      150                      155                      160 acc  tgc  agg  aca  gtg  ccc  ttc  agc  cag  act  ata  acc  cac  gaa  ggc  tgt    528
Thr  Cys  Arg  Thr  Val  Pro  Phe  Ser  Gln  Thr  Ile  Thr  His  Glu  Gly  Cys
                         165                      170                      175 gaa  aaa  gta  gtt  gtt  cag  aac  aac  ctt  tgc  ttt  ggg  aaa  tgc  ggg  tct    576
Glu  Lys  Val  Val  Val  Gln  Asn  Asn  Leu  Cys  Phe  Gly  Lys  Cys  Gly  Ser
```

<110> APPLICANT: Barbour, Eric
    EuClaire Meyer, Terry
    Eid Saad, Mohammed
<120> TITLE OF INVENTION: Novel Maize Promoters
<130> FILE REFERENCE: 5718-72
<140> CURRENT APPLICATION NUMBER: US/09/784,403
<141> CURRENT FILING DATE: 2001-02-15
<150> PRIOR APPLICATION NUMBER: 09/410,935
<151> PRIOR FILING DATE: 1999-10-04
<160> NUMBER OF SEQ ID NOS: 4
<170> SOFTWARE: FastSEQ for Windows Version 3.0

<210> SEQ ID NO 1
<211> LENGTH: 613
<212> TYPE: DNA
<213> ORGANISM: Zea mays
<220> FEATURE:
<221> NAME/KEY: promoter
<222> LOCATION: (0)...(0)
<223> OTHER INFORMATION: Actin-2

<400> SEQUENCE: 1

```
tcagtatgat tgctttcaat ataggctgat ggagcctatg aatgatctat aactatgtga     60
ttggatgtct taacttgcgt agccaagctc gtatgagcct cttttactgg gtaccactaa    120
tttctatata ttagatacag ttaaataagt ctaaattaca tcggtgcgtg cgtgccagta    180
cgactagatg tagtgaacta aacacaggtt aagctgtgat caatgtatgt agagagtctg    240
actctttata tgcggacaac taaacacacg ataagtgtcg agaatgattg aggaaatatt    300
ggtcgttcca cgtgattgag taagaatgag agggaaataa aaggatttgg tgcgttggtt    360
ttgaaggcag gatttggtta ggatgggtgg acgtttgaag tgatgagttt tcaagcgta     420 tagattttct atttgtcctt tttaattaac tttctcccag ccgggatgcg cgtataaaaa    480
ccggcgaaac ccttggctct cctcattcgg cctatcacaa ccgcttactc tcgtgcgctc    540
tccgtgggag cgaggacccg cggccggcgg cagcggcagc ttctcctaga tctccggcat    600
catcagtgga tcc                                                      613
```

```
<210> SEQ ID NO 2
<211> LENGTH: 664
<212> TYPE: DNA
<213> ORGANISM: Zea mays
<220> FEATURE:
<221> NAME/KEY: promoter
<222> LOCATION: (0)...(0)
<223> OTHER INFORMATION: Enolase

<400> SEQUENCE: 2
tcatatattt atgaacggag atagtgcatc tatcatgcga ttcttcgacg gagtcgacgt      60
ctgattggac cagaatttca gatggtgagc aaaagtgcca cttgcctgcc tccttttctc    120
gtgcctgcct aacacgtgcc tttgatctct agggcagtta taattaagac aagcaggtta    180
tattataagt caaggataga aagaaaggag aaacaatata ctatttaaga tcagataaaa    240
aaagagctaa taattttttg ggacacatat actggttaca ttgttataat ctgtatatat    300
cacgttgttc gaatatattc caaattttta ctatgattcg tgctctaccg gaactacttc    360
tagattttga aaactttatg agaattttct tatttagata cactaaggct aatttttggtt    420 ggttttttggc tcgctagcta ccattacctc ctgcatctag acattacaaa tttacaataa    480
ataaagttcc tagatttga acgaaaccag cagagcgcac accgtccttg ccccacggaa    540
caagaaaaat ggaatatgct cccgcagccc tcgtggaaac caagggcgga ccttcccctc    600
ctccaagcaa atccgaggcc cacccacggg ccgctcgaac atctgtcacc gccaagtggg    660
atcc                                                                  664

<210> SEQ ID NO 3
<211> LENGTH: 862
<212> TYPE: DNA
```